(12) United States Patent
Nagasaka

(10) Patent No.: US 10,188,507 B2
(45) Date of Patent: Jan. 29, 2019

(54) INTRAOCULAR LENS INJECTION SYSTEM AND CONTROLLER FOR CONTROLLING INTRAOCULAR LENS INJECTION DEVICE

(71) Applicant: NIDEK CO., LTD., Gamagori-shi, Aichi (JP)

(72) Inventor: Shinji Nagasaka, Toyota (JP)

(73) Assignee: NIDEK CO., LTD., Gamagori (JP)

( * ) Notice: Subject to any disclaimer, the term of this patent is extended or adjusted under 35 U.S.C. 154(b) by 175 days.

(21) Appl. No.: 15/224,024

(22) Filed: Jul. 29, 2016

(65) Prior Publication Data

US 2017/0027686 A1 Feb. 2, 2017

(30) Foreign Application Priority Data

Jul. 31, 2015 (JP) .................. 2015-151627
Jun. 21, 2016 (JP) .................. 2016-122295

(51) Int. Cl.
| | |
|---|---|
| A61F 2/16 | (2006.01) |
| A61F 9/00 | (2006.01) |
| A61F 9/007 | (2006.01) |
| A61F 9/008 | (2006.01) |
| A61B 90/00 | (2016.01) |

(52) U.S. Cl.
CPC ............ *A61F 2/167* (2013.01); *A61F 9/0061* (2013.01); *A61F 9/00736* (2013.01); *A61B 2090/3735* (2016.02); *A61F 2009/00851* (2013.01)

(58) Field of Classification Search
CPC .... A61F 2009/00851; A61F 2009/0052; A61F 2009/00844; A61F 2090/3735; A61F 3/00; A61F 2/16; A61F 2/1662; A61F 2/1664; A61F 2/1667; A61F 2/1672; A61F 2/167; A61F 9/00736; A61F 9/0061; A61F 9/007; A61F 9/0008; A61F 9/0017; A61F 9/0026; A61F 9/00727; A61F 9/00812; A61F 9/00834; G06T 7/0012
USPC .......................................................... 623/6
See application file for complete search history.

(56) References Cited

U.S. PATENT DOCUMENTS

| | | | | |
|---|---|---|---|---|
| 2010/0094309 A1* | 4/2010 | Boukhny | ............... | A61F 2/1662 606/107 |
| 2011/0279821 A1* | 11/2011 | Brennan | ................ | A61B 3/102 356/479 |

FOREIGN PATENT DOCUMENTS

| | | |
|---|---|---|
| EP | 2343029 A1 | 7/2011 |
| JP | 2011-139863 A | 7/2011 |

\* cited by examiner

*Primary Examiner* — Eric Rosen
*Assistant Examiner* — Chima Igboko
(74) *Attorney, Agent, or Firm* — Oliff PLC

(57) ABSTRACT

An intraocular lens injection system, a controller to control an intraocular lens injection device, a method for controlling an intraocular lens injection instrument, and a program therefor for preferably injecting an intraocular lens are provided. A push-out member including a drive part to push out a soft intraocular lens by the drive part, an observation member to obtain an observed image of the intraocular lens pushed out by the push-out member, and a determination member to determine a drive parameter of the drive part based on the observed image are provided. The intraocular lens includes an optical part and a support part to support the optical part in a patient's eye, and the determination member determines the drive parameter according to at least a shape of the support part.

6 Claims, 9 Drawing Sheets

(a)

(b)

(c)

(d)

(e)

INTRAOCULAR LENS INJECTION SYSTEM AND CONTROLLER FOR CONTROLLING INTRAOCULAR LENS INJECTION DEVICE

CROSS-REFERENCE TO RELATED APPLICATIONS

This application is based upon and claims the benefit of priority from the prior Japanese Patent Applications No. 2015-151627 filed on Jul. 31, 2015 and No. 2016-122295 filed on Jun. 21, 2016, the entire contents of which are incorporated herein by reference.

BACKGROUND

The present disclosure relates to an intraocular lens (IOL) injection system to inject an IOL into a patient's eye, a controller for injecting the IOL, a control method for an IOL injection instrument, and a control program therefor.

An IOL injection instrument for injecting an IOL into a patient's eye has been known. For example, an IOL injection instrument disclosed in Patent Document 1 is configured to deform an optical part and a support part of the IOL inside an injection part of the instrument and then inject the IOL.

RELATED ART DOCUMENTS

Patent Documents

Patent Document 1: JP-A-2011-139863

SUMMARY

When an IOL is deformed by an IOL injection device (such as an IOL injection instrument), the IOL is sometimes deformed inappropriately. In one example, when the IOL injection device pushes the inappropriately deformed IOL, the IOL may be partly damaged. In another example, when the IOL injection device injects the inappropriately deformed IOL into a patient's eye, an operator may require long time for setting the IOL. Further in another example, when the IOL injection device injects the inappropriately deformed IOL into the patient's eye, the IOL may cause damage to a tissue (such as a lens capsule, a cornea, and an iris) of the patient's eye.

In another example, a pushing force of the IOL injection device to push out the IOL may cause damage to the patient's eye. Specifically, when a part or the whole of the IOL has come out of the IOL injection device, the IOL brought into contact with a posterior capsule of a crystalline lens may cause damage to the posterior capsule due to the pushing force of the IOL injection device pushing the IOL.

The present disclosure has been made to provide an intraocular lens injection system, a controller for controlling an IOL injection device, a control method for an IOL injection instrument, and a control program therefor which are able to solve at least any one of the above problems and inject an IOL in an appropriate manner.

To solve the above problems, the present disclosure has the following configurations.

(1) An intraocular lens injection system for injecting an intraocular lens, the intraocular lens injection system comprising: a push-out member provided with a drive part to push out a soft intraocular lens by use of the drive part; an observation member to obtain an observed image of the intraocular lens which is pushed out by the push-out member; and a determination member to determine a drive parameter of the drive part based on the observed image.

(2) A controller for controlling an intraocular lens injection device comprising: a first interface configured to control a drive part for pushing out a soft intraocular lens; a second interface configured to input an observed image of the intraocular lens which is pushed out by the drive part; and a determination member configured to determine a drive parameter of the drive part based on the observed image.

(3) A control method for an intraocular lens injection device includes: a first step of inputting an observed image in which at least a part of an intraocular lens is included; a second step of detecting a shape of the intraocular lens by use of the observed image inputted in the first step; and a third step of determining a drive parameter of a drive part to push out the intraocular lens by use of a detection result obtained in the second step.

According to the present disclosure, an intraocular lens injection system, a controller for controlling an intraocular lens injection device, a control method of an intraocular lens injection instrument, and a control program therefor by which an intraocular lens can be appropriately injected are provided.

DETAILED DESCRIPTION OF THE EXEMPLARY EMBODIMENTS

Figure 1:
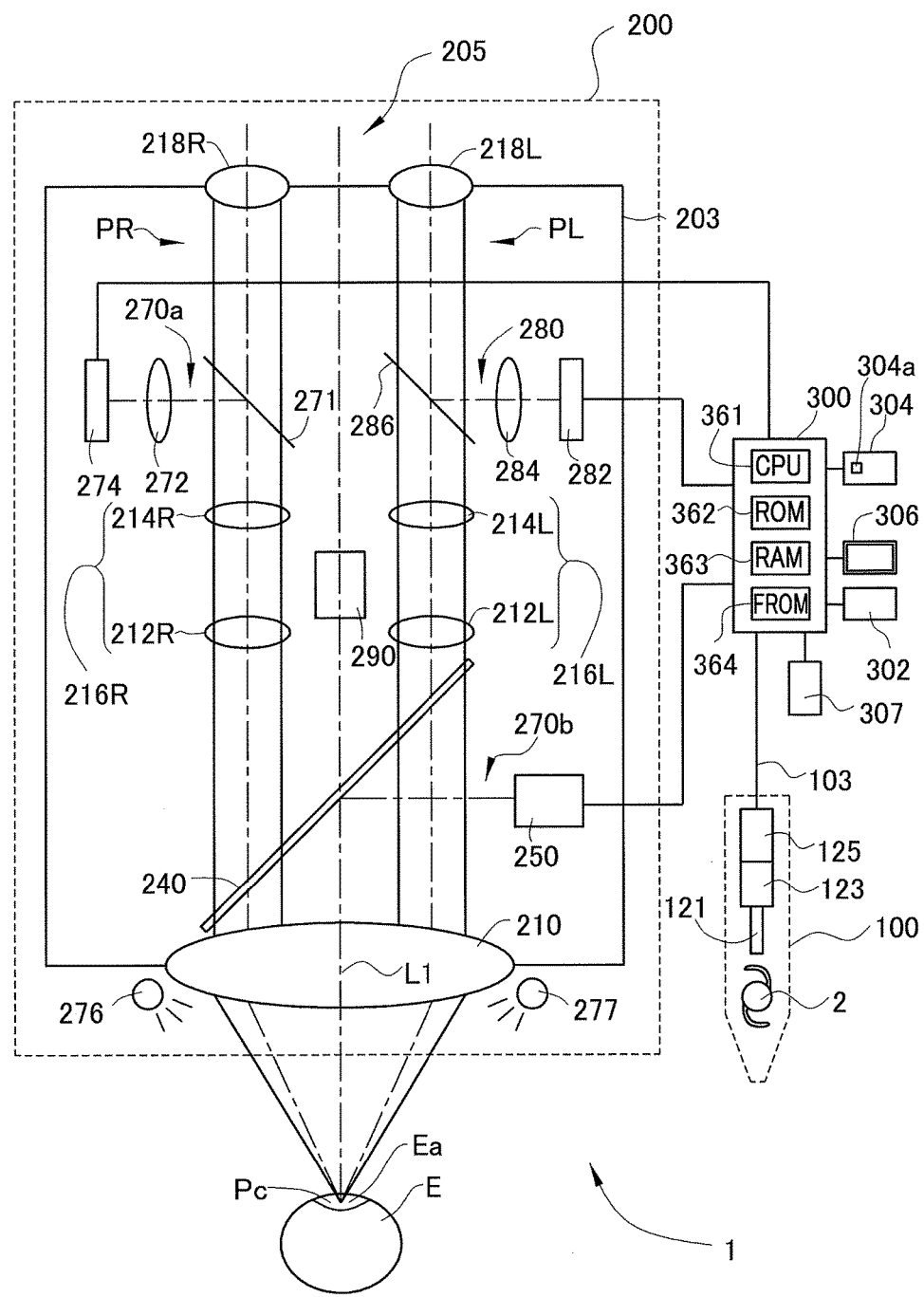
FIG. 1 is a schematic configurational view of an intraocular lens injection system of the present embodiment.

A typical embodiment of the present disclosure is now explained in detail with reference to the accompanying drawings. FIG. 1 is a schematic configurational view of an intraocular lens (IOL) injection system 1 of the present embodiment. The IOL injection system 1 of the present embodiment is configured to inject an IOL 2 as a substitute for a crystalline lens, which has been removed from a lens capsule, into a patient's eye E. An explanation for the present embodiment is given on condition that the IOL 2 injected into the patient's eye by the IOL injection system 1 is to be set in the lens capsule.

The IOL injection system 1 of the present embodiment includes an IOL injection device 100, a microscope unit 200, and a controller 300. The IOL injection device 100 of the present embodiment is configured to move the IOL 2 into the patient's eye from an outside of the eye. In other words, the IOL injection device 100 of the present embodiment is an injection member for the IOL 2. The microscope unit 200 of the present embodiment observes an anterior segment Ea of the patient's eye E, the IOL injection device 100, or the IOL 2. In other words, the microscope unit 200 of the present embodiment is an observation member for the patient's eye E, the IOL injection device 100, or the IOL 2. The controller 300 of the present embodiment controls the IOL injection device 100 or the microscope unit 200. In other words, the controller 300 of the present embodiment is a control member to control apparatuses (or instruments) engaged in injection of the IOL 2.

<Microscope Unit>

The microscope unit 200 of the present embodiment includes a microscope 205, an imaging optical system, a visual field display system 280, and the controller (control unit) 300. The microscope 205, the imaging optical system, and the visual field display system 280 of the present embodiment are embedded (housed) in a housing 203. The imaging optical system of the present embodiment includes a front-image imaging optical system 270a and a tomographic-image imaging optical system 270b. A user (an operator) uses the microscope 205 or the imaging optical system as one configuration of an observation optical system (i.e., an observation member) for observing the patient's eye E during a surgery.

The microscope 205 of the present embodiment includes an optical path PR extending from the patient's eye E to an operator's right eye and an optical path PL extending from the patient's eye E to an operator's left eye. The microscope 205 of the present embodiment is a binocular microscope (or may be a monocular microscope). The microscope 205 of the present embodiment includes an objective lens 210. In the present embodiment, the objective lens 210 is placed on a common optical path between the optical path PR and the optical path PL. In the present embodiment, a lens 212R, a lens 214R, and an eyepiece 218R are placed on the optical path PR, and a lens 212L, a lens 214L, and an eyepiece 218L are placed on the optical path PL. In the following explanation, an axis extending intermediate between the optical path PR and the optical path PL may be called as an axis L1.

In the present embodiment, a set of the lens 212R and the lens 214R and a set of the lens 212L and the lens 214L are each moved in a direction of an optical axis by a microscope drive part 290 and form a pair of zoom systems (a zoom system 216R and a zoom system 216L). A visible light source 277 of the present embodiment illuminates the anterior segment Ea of the patient's eye E with a visible light. In the present embodiment, the housing 203 is allowed to move in three axial directions (an upper and lower direction, a left and right direction, and a front and rear direction) by a not-shown arm. Specifically, the arm adjusts a position of the housing 203 such that the objective lens 210 is placed to be focused on the anterior segment Ea.

The visible light source 277 emits illumination light and this illumination light illuminates the anterior segment Ea from a front side. The illumination light reflected on the anterior segment Ea (i.e., reflection light) passes through (transmits) the objective lens 210 and a beam combiner 240. The light passing through the optical path PR then reaches the operator's right eye through the zoom system 216R, a dichroic mirror 271, and the eyepiece 218R. The light passing through the optical path PL reaches the operator's left eye through the zoom system 216L, a one-way mirror 286, and the eyepiece 218L. The operator looks into the eyepieces 218R and 218L with his right and left eyes, and thus he can observe a front image of the anterior segment Ea.

<Front-Image Imaging Optical System>

The front-image imaging optical system 270a of the present embodiment is configured to image (obtain) a front image IMGf of the anterior segment Ea. The front-image imaging optical system 270a of the present embodiment includes the objective lens 210, the zoom system 216R, the dichroic mirror 271, an imaging lens 272, and a light receiving element 274. The light receiving element 274 of the present embodiment is an image sensor (a two-dimensional imaging sensor). The light receiving element 274 of the present embodiment is arranged at a position substantially conjugate to the anterior segment Ea. The dichroic mirror 271 has the characteristics of reflecting an infrared light and transmitting the visible light. The front-image imaging optical system 270a of the present embodiment is configured to image the reflection light of the illumination light (the infrared light) emitted from the infrared light source 276, the illumination light being reflected on the patient's eye E. The front-image imaging optical system 270a of the present embodiment thus images the front image IMGf of the anterior segment Ea. Other than the anterior segment Ea, the front-image imaging optical system 270a of the present embodiment can also image the IOL 2 and the IOL injection device 100 placed within an imaging area.

Figure 2:
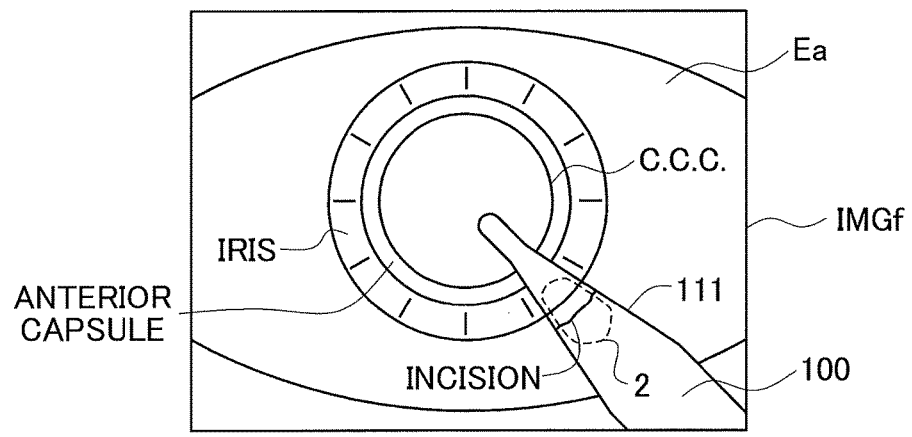
FIG. 2 is a front image of a patient's eye imaged by the intraocular lens injection system in FIG. 1.

FIG. 2 illustrates the front image IMGf imaged by the front-image imaging optical system 270a of the present embodiment. The front image IMGf shown in FIG. 2 includes the anterior segment Ea of the patient's eye E, the IOL injection device 10, the IOL 2, an incision formed on a cornea of the patient's eye E, C.C.C. (Continuous Curvicular Capslotomy) formed in an anterior capsule of the lens capsule, and others. The cartridge part 101 (see FIG. 4A) of the present embodiment is translucent (allowed to pass through the light), and thus it is possible to observe a shape of the IOL 2 which has been loaded inside the cartridge part 101 from an outside of the cartridge part 101.

An imaging member (an obtention member) for the front image IMGf is not limited to the above. For example, the front image IMGf may be imaged (obtained) by scanning laser beam. Any configuration may be adopted as long as the front image IMGf (a still image or a moving image) of the patient's eye E is imaged by the IOL injection system 1. The front image IMGf of the present embodiment is a monochrome image (an achromatic image), but alternatively, the front image IMGf may be a color image (a chromatic image).

<Tomographic-Image Imaging Optical System>

Figure 3:
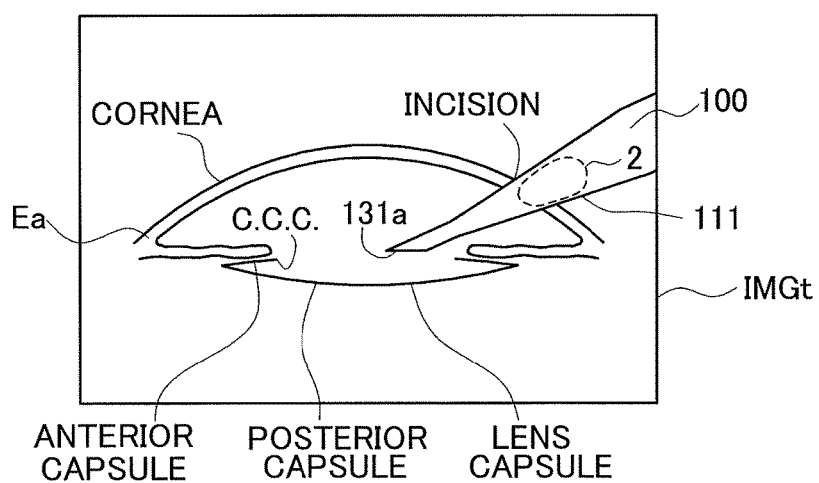
FIG. 3 is a tomographic image of the patient's eye imaged by the intraocular lens injection system in FIG. 1.

The tomographic-image imaging optical system 270b of the present embodiment is configured to, for example, obtain a tomographic image IMGt of the anterior segment Ea of the patient's eye E which is placed in a position for surgery. FIG. 3 illustrates the tomographic image IMGt imaged by the tomographic-image imaging optical system 270b of the present embodiment. The tomographic image IMGt in FIG. 3 includes the anterior segment Ea of the patient's eye E, the IOL injection device 100, the IOL 2, the cornea of the patient's eye E, the incision formed on the cornea of the patient's eye E, and others. As similar to the above mentioned front-image imaging optical system 270a, the tomographic-image imaging optical system 270b of the present embodiment makes it possible to observe a shape of the IOL 2 loaded inside the cartridge part 101 from an outside of the cartridge part 101.

The tomographic-image imaging optical system 270b of the present embodiment includes an OCT unit 250. The tomographic-image imaging optical system 270b uses the objective lens 210 in common with other optical systems. The OCT unit 250 is provided with an optical interferometer and an optical scanner, for example. The tomographic-image imaging optical system 270b of the present embodiment is configured to emit a measurement light on the patient's eye E. The tomographic-image imaging optical system 270b of the present embodiment is further configured to detect an interference state of the measurement light reflected on the patient's eye E and a reference light by use of the light receiving element (a detector).

The optical scanner of the present embodiment is an irradiation position changing unit to change an irradiation position of the measurement light on the patient's eye. In the present embodiment, the optical scanner enables to change an imaging position on the patient's eye E. The optical scanner of the present embodiment can perform scanning in a two-dimensional direction. The optical scanner of the present embodiment is connected to the controller 300. The controller 300 of the present embodiment controls movement of the optical scanner based on the set information of the imaging position and obtains the tomographic image IMGt based on a light receiving signal from the detector.

The tomographic image IMGt is specifically an image of a surface intersecting an imaging surface of the front image IMGf. In other words, the imaging surface of the front image IMGf and an imaging surface (a sectional surface) of the tomographic image IMGt intersect each other. To be more specific, the front image IMGf and the tomographic image IMGt are imaged (observed) objects (the patient's eye E, the IOL 2, the IOL injection device 100, and the like) each imaged from a different direction.

The tomographic-image imaging optical system 270b of the present embodiment has a configuration of a so-called Optical Coherence Tomography (OCT). The tomographic-image imaging optical system 270b is configured to, in one example, image the tomographic image IMGt of the anterior segment Ea of the patient's eye E while the IOL 2 is being injected into the patient's eye E. The tomographic-image imaging optical system 270b splits the light (the infrared light) emitted from a measurement light source into the measurement light (a sample light) and the reference light by a coupler (a beam splitter). The tomographic-image imaging optical system 270b subsequently introduces the measurement light to the patient's eye E and the reference light to a reference optical system. Subsequently, the detector (the light receiving element) receives a coherence light formed by synthesis of the measurement light reflected on the patient's eye E and the reference light.

The detector of the present embodiment detects an interference state of the measurement light and the reference light. For example, in an example of Fourier-domain OCT, a spectral intensity of the coherence light is detected by the detector and a depth profile (A scan signal) in a predetermined range is obtained by performing Fourier transform of spectral intensity data. As examples, Spectral-domain OCT (SD-OCT) and Swept-source OCT (SS-OCT) are employed as the OCT device. Another example is Time-domain OCT (TD-OCT). In an example of the SD-OCT, a low coherent light source (supercontinuum lasers) is used as a light source, and the detector is provided with a spectral optical system (a spectrometer) to disperse the coherent light into each frequency component (each wavelength component). The spectrometer is, for example, made up of a diffraction grating and a line sensor.

In an example of the SS-OCT, a wavelength scanning light source (a wavelength variable light source) to change an outgoing wavelength at temporally high speed is used as the light source, and a single light receiving element is provided as one example for the detector. The light source is, for example, configured with a light source, a fiber ring resonator, and a wavelength selectable filter. As the wavelength selectable filter, a combination of a diffraction grating and a polygon mirror or a Fabry-Perot Etalon filter may be employed. A configuration of an optical coherence tomography device is described in JP-A-2012-213634 and JP-A-2008-29467.

The front image IMGf of the patient's eye E may be imaged by the tomographic-image imaging optical system 270b (JP-A-2011-215134 refers to this configuration, for example). In this example, the microscope unit 200 may not include the front-image imaging optical system 270a. The configuration of the tomographic-image imaging optical system 270b is not limited to the exemplified configuration of the OCT device. The configuration may be the one other than the above example as long as the IOL injection system 1 enables to obtain the tomographic image IMGt (a still image or a moving image) of the patient's eye E. As one example, an optical system using Scheimpflug principle may be employed to observe the patient's eye E, the IOL 2, or the IOL injection device 100 from a direction different from a direction in which the front image IMGf is obtained.

<Visual Field Display System>

The visual field display system 280 is provided to display information related to a surgery in the visual field of the microscope 205. The visual field display system 280 includes a display part 282, a projection lens (a projection lens system) 284, and the one-way mirror 286. The display part 282 is, for example, embodied with a display device such as an LCD, an organic EL (OLED), and a liquid crystal projector. The one-way mirror 286 of the present embodiment is placed on the optical path PL and configured to synthesize the reflection light illuminated by the visible light source 277 and reflected on the patient's eye E with a projection light from the display part 282. In the present embodiment, the display part 282 is constituted of the LCD, and contents displayed by the display part 282 is controlled by the controller 300. The front image IMGf and the tomographic image IMGt may be displayed on the display part 282.

<Controller>

With reference to FIG. 1, the controller 300 of the present embodiment is explained. The controller 300 of the present embodiment controls the IOL injection system 1. The controller 300 of the present embodiment is provided with a CPU (a processor) 361, an ROM 362, an RAM 363, and a nonvolatile memory 364. The CPU 361 of the present embodiment is in charge of controlling each section of the IOL injection system 1. The controller 300 or the CPU 361 may be called as a computer. The ROM 362 of the present embodiment is stored with various program, initial values, and others. The RAM 363 temporarily stores various information. The nonvolatile memory 364 of the present embodiment is a non-fugitive storage medium which can retain storage contents even when supply of power source is shut off. Specifically, the ROM 362, the RAM 363, and the nonvolatile memory 364 are storage members to store data used for the computer.

The nonvolatile memory 364 may be embodied with, for example, a USB memory attached to the controller 300 in a detachable manner, a flash ROM embedded in the controller 300, and the like. The USB memory may be, in one example, utilized as a readable storage medium read out by the computer (the CPU 361). In this example, the USB memory stores a program to perform controlling of the IOL injection system 1 in the CPU 361 (the computer).

The controller 300 of the present embodiment is connected with components including the microscope drive part 290, the infrared light source 276, the visible light source 277, the OCT unit 250, the light receiving element 274, the display part 282, a memory 302, an operation part 304, an external display 306, a foot pedal 307, and the IOL injection device 100. The operation part 304 is manually operated. The operator is, for example, allowed to set operating conditions of the IOL injection device 100 by using the operation part 304. The foot pedal 307 is operated by the operator as a trigger for starting injection of the IOL 2, for example. The controller 300 of the present embodiment obtains the tomographic image IMGt based on an output signal from the OCT unit 250 and the front image IMGf based on an output signal from the light receiving element 274. In other words, the controller 300 of the present embodiment has an interface to input an observed image (the front image IMGf or the tomographic image IMGt) of the IOL 2 which is being pushed by a drive part 125.

The controller 300 of the present embodiment controls the external display 306 to display at least any one of the front image IMGf obtained by the front-image imaging optical system 270a, the tomographic image IMGt obtained by the tomographic-image imaging optical system 270b, and any other information related to the surgery. Other information related to the surgery may include settings of the IOL injection device 100.

The controller 300 of the present embodiment analyzes the observed image (the front image IMGf or the tomographic image IMGt) obtained (inputted) from the microscope unit 200 and then detects the shape of the soft IOL 2 which is being pushed by a push member (a plunger). The controller 300 thus determines a drive parameter used for controlling the drive part 125 according to the detected shape of the IOL 2.

The controller 300 of the present embodiment includes, specifically, a first interface for controlling the drive part 125 (a drive member), a second interface for inputting the observed image (the front image IMGf or the tomographic image IMGt) of the IOL 2, and a determination member to detect the shape of the pushed out IOL 2 from the observed image and then determine a parameter used for controlling the drive part 125 according to the detected shape of the IOL 2.

The IOL injection device 100 of the present embodiment includes a stepper motor used as a driving source for the drive part 125. The controller 300 determines a control signal of the stepper motor of the drive part 125 according to the detected shape of the IOL 2. By this control signal, the controller 300 of the present embodiment determines the push-out speed (including ON (start operation)/OFF (stop operation)) of a plunger 121 which is driven by a driving force of the drive part 125.

The controller 300 of the present embodiment analyzes the observed image (the front image IMGf or the tomographic image IMGt) by a method of image processing. The controller 300 of the present embodiment utilizes the method of image processing for analyzing the shape of the IOL 2. The method of image processing is such as pattern matching, image binarization, and edge detection. When the pattern matching is used, template data used therefor may be stored in a memory such as the ROM 362 or the nonvolatile memory 364.

The controller 300 of the present embodiment analyzes the shape of the IOL 2 by specifically analyzing a longitudinal length (a length in a direction parallel to a push-out axis A) of the IOL 2 which is deformed by a deformation mechanism, a widthwise length (a length in a direction orthogonal to the push-out axis A) of the IOL 2 deformed by the deformation mechanism, a shape of the support part 4 (a front-side support part 4a or a rear-side support part 4b) (for example, a direction in which a distal end of the support part 4 faces), and others.

The controller 300 of the present embodiment thus determines the drive parameter used for controlling the drive part 125 according to the shape of the IOL 2. This determination of the drive parameter can prevent the IOL 2 from getting damaged while the IOL 2 is pushed out, for example. Further, this determination of the drive parameter can reduce burden of the operator to set the IOL 2 inside an eye after the IOL injection device 100 has injected the IOL 2 into the patient's eye E. Accordingly, even an operator who is inexpert in injection of the IOL 2 can perform injection of the IOL 2 into the patient's eye E promptly and further safely.

The IOL injection device 100 may be connected to other surgical apparatuses (an apparatus for cataract surgery or an apparatus for cataract vitreous surgery), for example. The microscope unit 200 outputs the observed image (the front image IMGf or the tomographic image IMGt). A control section included in the apparatus for cataract surgery may input and analyze the observed image, and may further determine the drive parameter of the drive member used for pushing out the IOL 2 according to the detected shape of the IOL 2. In this example, the surgical apparatus functions as the controller 300. As another example, a PC (a personal computer) may be configured to take in the observed image and the observed image is analyzed by a computer included in the PC to determine and output the drive parameter from the PC. In this example, the PC functions as the controller 300. As another example, the IOL injection device 100 embedded with a control part functions as the controller 300.

The controller 300 may detect the shape of the IOL 2 only by use of the front image IMGf. Only utilizing the front image IMGf enables to simplify the configuration of the IOL injection system 1. Utilizing the tomographic image IMGt to detect the shape of the IOL 2 in the controller 300 realizes preferable detection of a part of the IOL injection device 100 which has entered into the patient's eye E or the shape of the IOL 2. In the present embodiment, the OCT device is used for obtention of the tomographic image IMGt, thus simplifying the configuration of the optical system of the IOL injection system 1. The controller 300 may alternatively detect the shape of the IOL 2 only by use of the tomographic image IMGt. This example makes the configuration of the IOL injection system 1 simpler than the configuration in which the front image IMGf and the tomographic image IMGt are obtained by different optical systems.

<Injection Instrument Part>

Figure 4A:
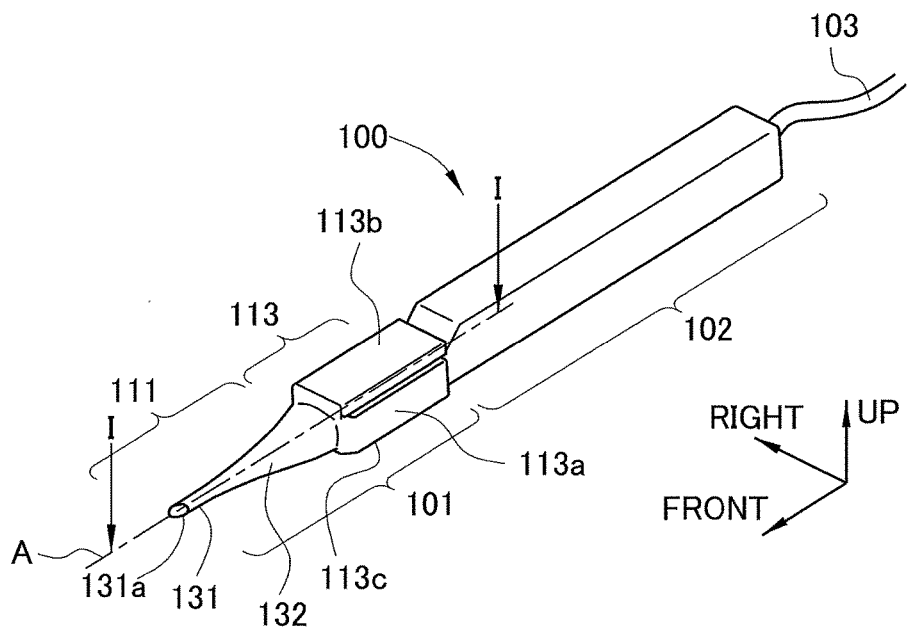
FIG. 4A is an external perspective view of an intraocular lens injection device used for the intraocular lens injection system in FIG. 1.
Figure 4B:
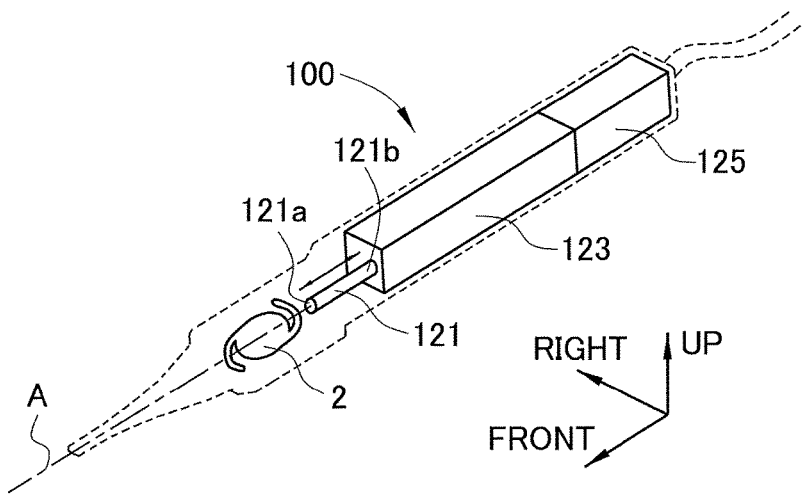
FIG. 4B is a schematic configurational view for explaining an inner configuration of the intraocular lens injection device.

The IOL injection device 100 of the present embodiment is now explained with reference to FIGS. 4A, 4B, and 5. FIG. 4A is an external perspective view of the IOL injection device 100 of the present embodiment when seeing the device from an upper side. FIG. 4B is a schematic configurational view for explaining an inner configuration of the IOL injection device 100 of the present embodiment. The IOL injection device 100 of the present embodiment is configured to move the IOL 2 from an outside to an inside of the patient's eye E. In other words, the IOL injection device 100 of the present embodiment is an injection member for the IOL 2.

The IOL injection device 100 of the present embodiment is provided with the cartridge part 101 and a handpiece part 102. The cartridge part 101 of the present embodiment is attached to the handpiece part 102 in a detachable manner. In the present embodiment, the operator attaches the cartridge part 101 to the handpiece part 102 when the IOL 1 is about to be injected into the patient's eye E.

At least a part of the cartridge part 101 of the present embodiment is inserted through an incision formed in a sclera (or the cornea) of the patient's eye E. The cartridge part 101 of the present embodiment includes a deformation mechanism to deform the IOL 2 (which will be explained below). The handpiece part 102 of the present embodiment includes a power-driven member to move the IOL 2 from an outside to an inside of the patient's eye E.

The cartridge part 101 is replaced for every use in the IOL injection device 100 of the present embodiment. The cartridge part 101 of the present embodiment is a so-called disposable type (a throwaway cartridge). The once used cartridge part 101 is disposed by a user (an operator or an assistant), for example. The IOL injection device 100 of the present embodiment uses a new cartridge part 101 for each patient's eye E. The IOL 2 has been loaded on the cartridge part 101 of the present embodiment in advance. The operator selects the cartridge part 101 loaded with the IOL 2 which corresponds to the eye characteristics of the patient's eye E and attaches the selected cartridge part 101 to the handpiece part 102. As one alternative, the IOL 2 may be loaded on the IOL injection device 100 at the site of use.

The IOL injection device 100 of the present embodiment is connected to the controller 300 via a cable 103. In the present embodiment, motive power of the IOL injection device 100 to move the IOL 2 is supplied by the controller 300 through the cable 103. As another example, the IOL injection device 100 may be provided with a battery. As another example, the controller 300 and the IOL injection device 100 may be wirelessly connected.

<Intraocular Lens>

Figure 5:
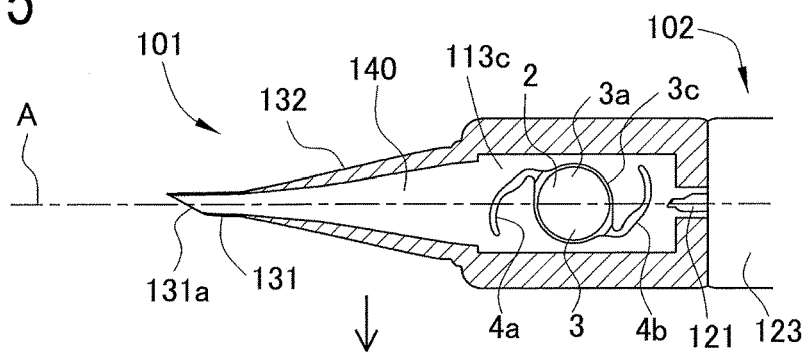
FIG. 5 is an explanatory view explaining deformation of an intraocular lens.
Figure 5:
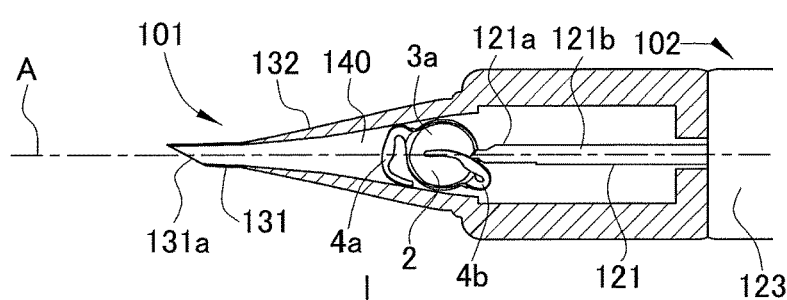
Figure 5:
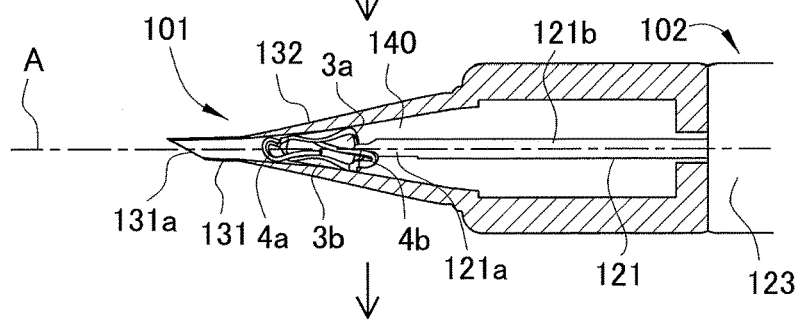
Figure 5:
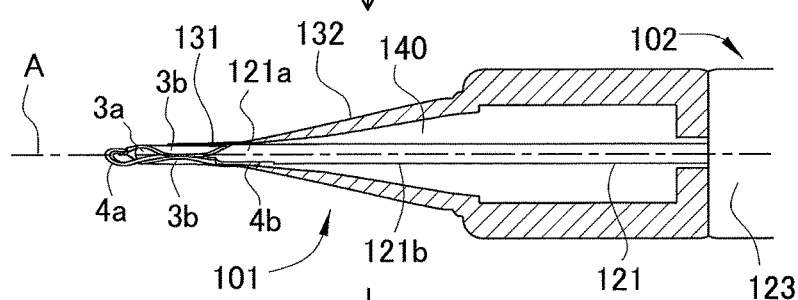
Figure 5:
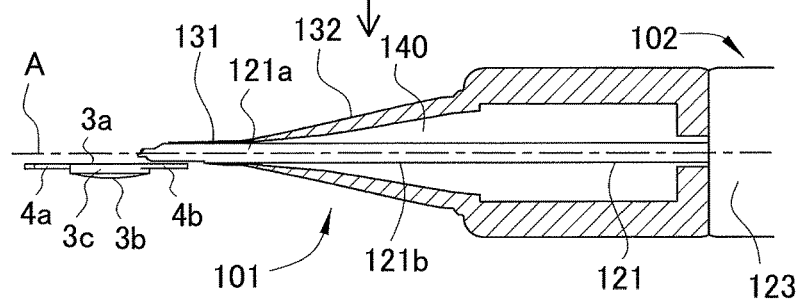

Further referring to FIG. 5, the intraocular lens (IOL) 2 which is to be injected by the IOL injection system 1 of the present embodiment is explained. The IOL 2 of the present embodiment includes, as one example, an optical part 3 and the support part 4. In the present embodiment, the optical part 3 and the support part 4 are integrally formed (which is sometimes called as a one-piece IOL). The IOL 2 of the present embodiment is a soft IOL. For forming the IOL 2, material such as a single substance such as HEMA (hydroxyethyl methacrylate) or composite material of acrylate ester and methacrylate ester, which have been used for conventional foldable (allowed to be curved) soft IOLs, may be used.

The optical part 3 of the present embodiment applies a predetermined refraction force to the patient's eye E. In the present embodiment, the optical part 3 is connected with the support part 4 at its peripheral portion so that the optical part 3 is supported in the eye. The IOL 2 of the present embodiment is provided with a pair of the support parts 4 (the front-side support part 4a and the rear-side support part 4b). In the present embodiment, the support part 4 facing toward a nozzle portion 131 when the IOL 2 is placed on a setting face 113c (which will be explained below) is called as the front-side support part 4a, and the support part 4 facing toward the plunger 121 is called as the rear-side support part 4b.

Each support part 4 extends outward from the peripheral portion (an optical-part side face 3c) of the optical part 3. The support parts 4 of the present embodiment are each curved in a circumferential direction to form a loop-like shape. A distal end of each support part 4 is a free end (this type of the support part is sometimes called as an open-loop support part). The pair of the support parts 4 are formed symmetrically with respect to a center (an optical axis) of the optical part 3 and extend in the same circumferential direction. The optical part 3 of the IOL 2 of the present embodiment includes a front-face optical surface 3a, a rear-face optical surface 3b, and the optical-part side face 3c. The IOL 2 of the present embodiment has different bending forces in the front-face optical surface 3a and the rear-face optical surface 3b, for example. The front-face optical surface 3a of the present embodiment is configured to face toward the cornea in the eye, and the rear-face optical surface 3b is configured to face toward a retina in the eye. The optical-part side face 3c of the present embodiment connects the front-face optical surface 3a and the rear-face optical surface 3b.

A configuration of the IOL is not limited to the above. As one alternative, a three-piece IOL may be used. The three-piece IOL is formed by an optical part and a support part which are made of different components (different materials). The support part of the three-piece IOL is, for example, in a string-like shape. As another alternative, a plate-type IOL may be used. A support part of the plate-type IOL is, for example, in a plate-like shape. As another alternative, an IOL with no support part may be used.

<Cartridge Part>

With reference to FIGS. 4A and 4B, the cartridge part 101 of the present embodiment is explained. The cartridge part 101 of the present embodiment is formed by injection molding using resin material. The cartridge part 101 of the present embodiment is in a cylindrical shape. The cartridge part 101 of the present embodiment is provided with a hollow portion 140 extending through the cartridge part 101 from its proximal end to its distal end (see FIG. 5). The cartridge part 101 is provided with an injection portion 111 and a setting portion 113. The cartridge part 101 of the present embodiment is translucent. Namely, the cartridge part 101 is allowed to pass the light. Accordingly, imaging members (the front-image imaging optical system 270a and the tomographic-image imaging optical system 270b) of the microscope unit 200 can observe (image) the shape of the IOL 2 stored inside the cartridge part 101 from an outside of the cartridge part 101.

The injection portion 111 of the present embodiment is injected its leading end into the incision formed in the cornea of the patient's eye E. The injection portion 111 of the present embodiment includes the nozzle portion 131 and a tapered portion 132. The nozzle portion 131 of the present embodiment has openings on its both ends to form a hollow cylindrical shape. The nozzle portion 131 of the present embodiment is provided with a bevel 131a at its leading end. The bevel 131a of the present embodiment has an end face formed inclined relative to a sectional face orthogonal to the push-out axis A. In FIG. 4A, the end face of the bevel 131a is oriented leftward with respect to the face orthogonal to the push-out axis A. The IOL injection device 100 of the present embodiment is configured to direct the end face of the bevel 131a toward the retina of the patient's eye E to inject the IOL 2.

The proximal end of the nozzle portion 131 is continuously formed with the tapered portion 132. The tapered portion 132 of the present embodiment is in a cylindrical shape. An inner hollow shape of the tapered portion 132 is tapered toward its distal end. In the present embodiment, the IOL 2 is folded into a tiny piece by the thus tapered inner shape of the tapered portion 132. In the present embodiment, the front-side optical surface 3a is valley-folded. The proximal end of the tapered portion 132 is connected with the setting portion 113. The IOL 2 which is to be pushed by the plunger 121 (which will be explained below) is placed (set) on the setting portion 113. The setting portion 113 of the present embodiment is provided with a setting body 113a, a setting cover 113b, and the setting face 113c.

The setting cover 113b is rotatable relative to the setting body 113a. When the setting cover 113b is closed, a cylindrical inner hollow space (the hollow portion 140) is formed in the setting portion 113. The cartridge part 101 of the present embodiment is configured to load the IOL 2 by opening the setting cover 113b. To be specific, a user or a manufacturer temporarily opens the setting cover 113b and disposes the IOL 2 on the setting face 113c. The setting cover 113b is then closed, and the loaded IOL 2 is engaged inside the setting portion 113 by an engagement mechanism. At the site of use, the IOL 2 is injected while the setting cover 113b is closed.

<Handpiece Part>

A housing of the handpiece part 102 of the present embodiment is made of metal. The handpiece part 102 of the present embodiment has a drive member to move the IOL 2. The drive member moves the IOL 2 into the patient's eye E from outside. The handpiece part 102 of the present embodiment includes the plunger 121, a power conversion part 123, and the drive part 125. The plunger 121 of the present embodiment is configured to be in contact with the IOL 2 to push the IOL 2. The plunger 121 of the present embodiment is a bar-like component. The plunger 121 of the present embodiment includes a tip end 121a and a base 121b. A leading end of the plunger 121 is provided with the tip end 121a. The tip end 121a of the present embodiment is configured to be in contact with the IOL 2 to push the IOL 2.

A proximal end side of the tip end 121a is continuously formed with the base 121b. A proximal end of the base 121b is connected with the power conversion part 123. The plunger 121 of the present embodiment is moved along the push-out axis A by the power generated in the drive part 125. The controller 300 gives control signals and controls the plunger 121 of the present embodiment to move toward a leading end of the push-out axis A (move forward) or move toward a proximal end of the push-out axis A (move backward).

The power conversion part 123 of the present embodiment includes a conversion mechanism. The conversion mechanism of the present embodiment converts a rotational movement generated by the stepper motor (which will be explained below) into a straight forward movement (movement in a direction parallel to the push-out axis A). The plunger 121 is connected with the conversion mechanism of the power conversion part 123. To a proximal end of the power conversion part 123, the drive part 125 is connected. In the present embodiment, the stepper motor is used as the drive part 125. A rotary shaft of the stepper motor is connected to the conversion mechanism of the drive part 125. The drive part 125 and the controller 300 are connected via the cable 103. The cable 103 of the present embodiment is used as an interface to control the drive part 125 for pushing out the soft IOL 2.

The controller 300 of the present embodiment enables to control each of a rotation direction, a rotation angle, and a rotation amount of the shaft of the stepper motor. The controller 300 thus detects a moving distance (on the push-out axis A) of the tip end 121a. Further, the controller 300 of the present embodiment detects a flow rate of the current consumed by the stepper motor. The controller 300 of the present embodiment further analyzes changes in the flow rate of the current consumed by the stepper motor and detects moving load of the plunger 121. To be more specific, the controller 300 of the present embodiment detects the moving load of the plunger 121, and therefore the controller 300 can detect the load (stress or the like) to which the IOL 2 is subjected during moving (or not moving). The IOL 2 which is being pushed out is subjected to stress by a viscoelastic substance injected into the cartridge part 101, a frictional force between the IOL 2 and an inner wall surface defining the hollow portion 140, and others.

<Preparation for Injecting the IOL>

Figure 9:
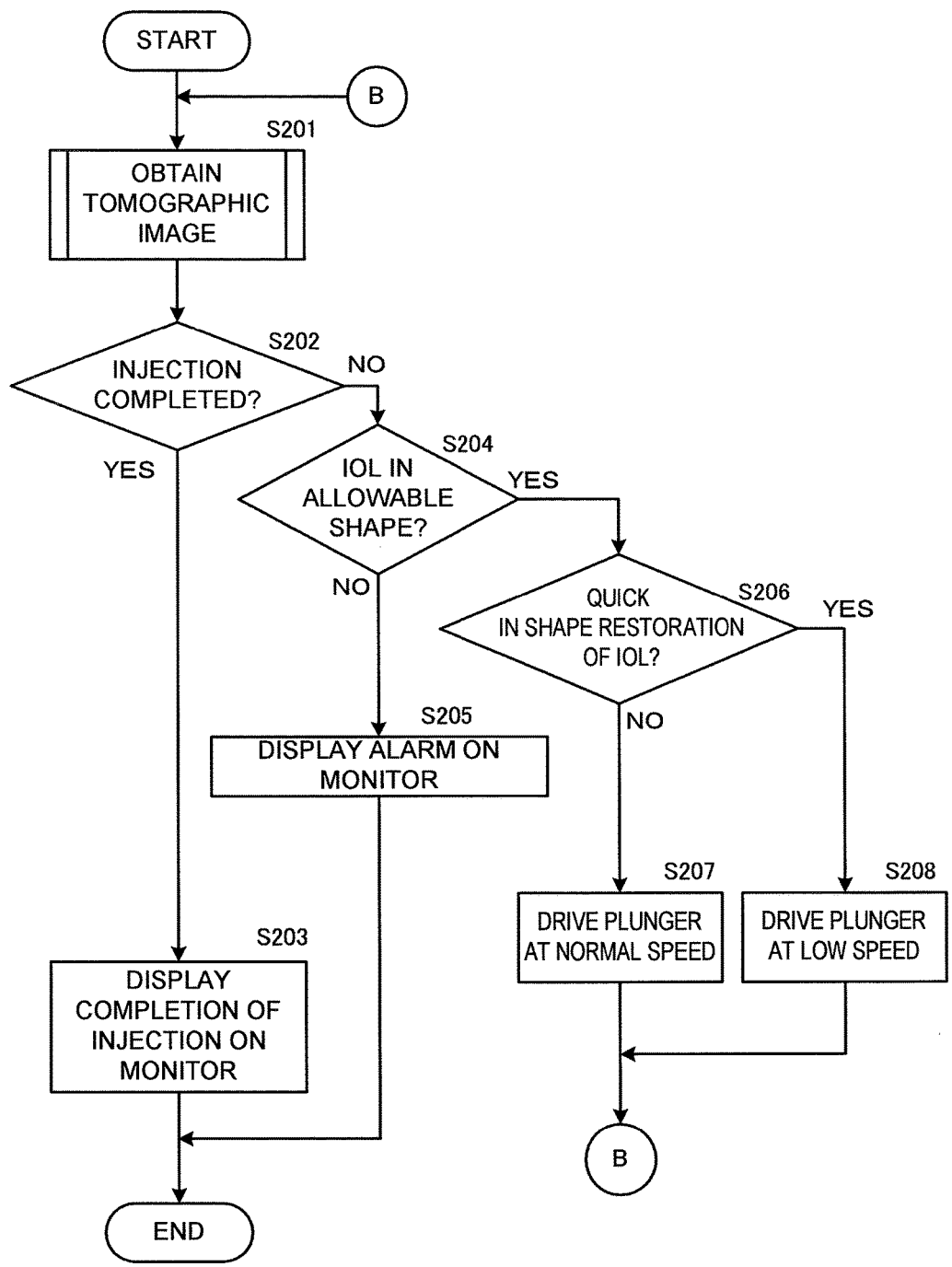
FIG. 9 is a flow chart for injecting the intraocular lens.
Figure 10:
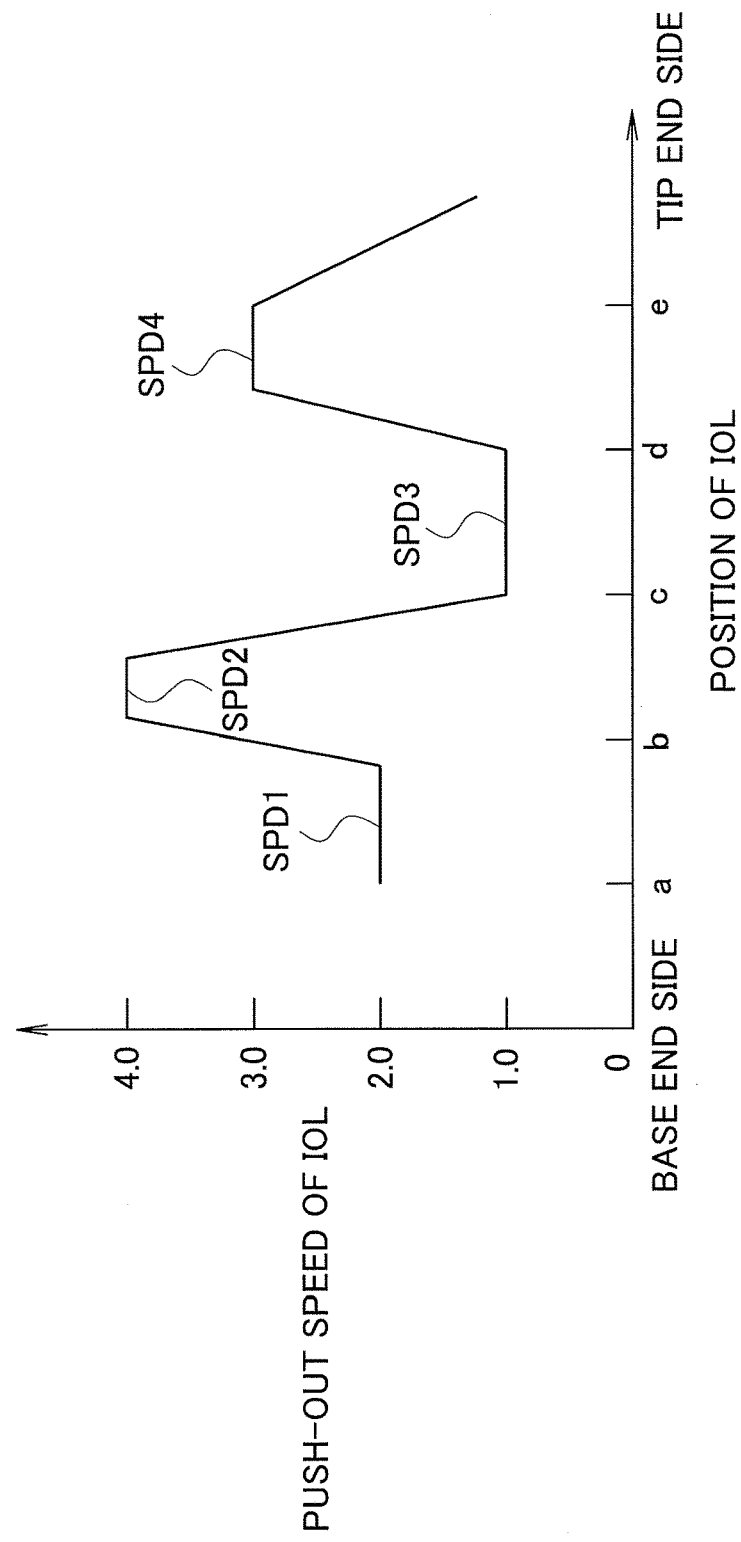
FIG. 10 is a graph for explaining a push-out speed.

With reference to FIGS. 5 to 10, a process (in one example) of an IOL injection surgery using the IOL injection system 1 of the present embodiment is explained. Each of states (a) to (e) in FIG. 5 is a sectional view taken along a line I-I in FIG. 4A, and more specifically, a partial sectional view in which a housing part of the cartridge part 101 is shown for explanation. In explaining an injection operation of the IOL 2, it is assumed that the operator operates the controller 300 to move the plunger 121 in the order of the states (a) to (e) in FIG. 5. In FIG. 10, a horizontal axis indicates a moving position of the IOL 2. Horizontal-axis labels (alphabets) "a" to "e" in FIG. 10 represent the positions of the IOL in the states (a) to (e) of FIG. 5, respectively. In FIG. 10, a vertical axis indicates a push-out speed of the IOL. Vertical-axis labels (numerals) in FIG. 10 are relative values when a speed SPD3 is assumed as 1.0.

The operator firstly makes a patient lie on his back on an operating table so that the patient's eye E is placed in a position for surgery. The operator holds the IOL injection device 100 with his left hand. At this time, the cartridge part 101 has not been mounted in the IOL injection device 100 yet. The operator operates the operation part 304 with his right hand to select an injection mode for injecting the IOL 2. Further, the operator inputs a type (for example, a model number) of the cartridge part 101 to be used. When the injection mode is selected, the controller 300 controls the plunger 121 to move backward to an initial position (a position in the state (a) of FIG. 5).

The operator confirms that the plunger 121 has moved back to the initial position and then attaches the cartridge part 101 to the handpiece part 102 (a state shown in the state (a) in FIG. 5). The operator attaches the cartridge part 101, which has been loaded with the IOL 2 corresponding to an eyesight of the patient's eye E, to the handpiece part 102. Subsequently, the operator uses a syringe or the like to inject a viscoelastic substance (a lubricant) into the hollow portion 140 of the cartridge part 101.

Subsequently, the operator presses down the foot pedal 307 to a first stage (a first inclination angle) to bring the IOL 2 to a waiting position (the state (c) in FIG. 5). The controller 300 detects pressing of the foot pedal 307 and then moves the plunger 121 at a predetermined speed until the IOL 2 reaches the waiting position (see steps S101 and S103 in FIG. 8). At this time, the controller 300 of the present embodiment controls to push out the IOL 2 at a speed SPD1 until the IOL 2 enters in the tapered portion 132 (see a section from a to b in FIG. 10). The controller 300 of the present embodiment further detects a moving amount (an advancing amount) of the plunger 121. The controller 300 further estimates a moving position of the IOL 2 from the detected moving amount of the plunger 121. As one alternative, the controller 300 may analyze the front image IMGf or the tomographic image IMGt and thereby detect the moving position of the IOL 2.

Before the IOL 2 enters in the tapered portion 132, the rear-side support part 4*b* is folded about its root or proximal portion by contact with the plunger 121. A distal end of the folded rear-side support part 4*b* is thus directed to the forward of the push-out axis A. Namely, the rear-side support part 4*b* has been tucked on the optical part 3. In the present embodiment, when the rear-side support part 4*b* is tucked, the distal end of the rear-side support part 4*b* faces the front-face optical surface 3*a*. As mentioned below, the front-side support part 4*a* will also be tucked on the same optical surface (the front-face optical surface 3*a*) in the tapered portion 132.

The plunger 121 comes to contact with the optical part 3 with the rear-side support part 4*b* being tucked. The plunger 121 pushes the whole IOL 2 to the forward of the push-out axis A. When the whole IOL 2 enters in the tapered portion 132, the optical part 3 is gradually deformed into a curved shape when seen from the rearward of the push-out axis A (see the state (b) in FIG. 5). Further, the distal end of the front-side support part 4*a* is deformed to come close to the optical part 3. When the IOL 2 enters in the tapered portion 132, the controller 300 of the present embodiment controls the push-out speed to push the IOL 2 to increase to the speed SPD2 once and then decrease to the speed SPD 3 to bring the IOL 2 in the waiting position (see a section from a to c in FIG. 10). Those push-out speeds to push the IOL 2 are set to a relationship expressed by the speed SPD1<the speed SPD2 and further by the speed SPD2>the speed SPD3. The controller 300 of the present embodiment increases the push-out speed at the timing when the IOL 2 enters in the tapered portion 132, thereby preventing unintentional deformation of the IOL 2 in the tapered portion 132 where the IOL 2 is deformed with a large deformation amount. To be specific, the controller 300 increases the push-out speed to the speed SPD2 to further increase the stress (such as the frictional force or the resilient force) applied by the tapered shape to bring the support part 4 (the front-side support part 4*a*) closer to the optical part 3. Accordingly, for example, tucking failure of the support part 4 (for example, a case that the support part 4 fails to move on the optical part 3) is restrained. After the support part 4 is tucked, the controller 300 of the present embodiment decreases the push-out speed from the speed SPD2 to the speed SPD3 so that sudden change in the stress applied to the IOL 2 is restrained. In other words, unintentional deformation of the IOL 2 is prevented.

The IOL 2 is gradually folded into a tiny piece as the plunger 121 moves toward the forward of the push-out axis A. When the IOL 2 reaches the waiting position, the controller 300 controls the plunger 121 to halt its movement (advancing) (see the state (c) in FIG. 5). In the IOL 2 having reached the waiting position, the front-side support part 4*a* and the rear-side support part 4*b* are tucked on the optical part 3, and the optical part 3 is entirely folded into a tiny piece (see (c) in FIG. 5). In other words, the cartridge part 101 of the present embodiment deforms the whole optical part 3 while enclosing the front-side support part 4*a* and the rear-side support part 4*b*.

As mentioned above, the controller 300 uses the control signal transmitted to the drive part 125 to successively detect the moving position of the plunger 121. The controller 300 also uses the control signal transmitted to the drive part 125 to successively detect the moving load of the plunger 121. When the controller 300 detects that the moving load of the plunger 121 exceeds a predetermined amount while the IOL 2 is moved from the initial position ((a) in FIG. 5) to the waiting position ((c) in FIG. 5), the controller 300 controls the plunger 121 to stop advancing (stops driving the plunger 121) and causes a buzzer to generate a notification sound. At this time, the controller 300 controls the external display 306 to display a message indicating an abnormal state (excess in the moving load) being detected. As one alternative to the above, the controller 300 may determine the state as abnormal when the moving load of the plunger 121 is less than the predetermined amount.

When the IOL 2 has reached the waiting position, the operator places the cartridge part 101 on a focus position of the objective lens 210. The controller 300 controls the front-image imaging optical system 270*a* to obtain the front image IMGf including an image of the cartridge part 101 (see a step S102 in FIG. 8). The controller 300 then controls the external display 306 to display the obtained front image IMGf. At this time, the controller 300 may successively renew the front image IMGf displayed on the external display 306 (or the external display 306 may display moving images).

The controller 300 detects the shape (such as an outline) of the IOL 2 by processing the obtained front image IMGf. The controller 300 then determines the detected shape of the IOL 2. When the controller 300 determines the IOL 2 as in an allowable shape, the external display 306 shows the corresponding message (for example, shows the message of "injection is allowed"). On the contrary, when the controller 300 determines the IOL 2 as not in the allowable shape, the external display 306 shows the corresponding message (for example, shows an alarm message of instructing replacement of the cartridge part 101) (see a step S105 in FIG. 8).

When it is determined that the IOL 2 is not in the allowable shape, the controller 300 may control the external display 306 to alternatively display a method of replacing the cartridge part 101. When it is determined that the IOL 2 is not in the allowable shape, the controller 300 controls the plunger 121 to move back to the initial position. The operator confirms the message displayed on the external display 306 and then replaces the cartridge part 101. After that, the operator performs the above mentioned operation again and moves the IOL 2 to the waiting position.

As mentioned above, specifically, the controller 300 of the present embodiment analyzes the shape of the IOL 2 having reached the waiting position and determines whether or not the IOL 2 is allowed to be continuously pushed out. Namely, the controller 300 of the present embodiment is a determination member to detect the shape of the IOL 2 from the observed image and to determine the drive parameter for the drive part 125 from the detected result. The controller 300 may input the detection result to determine the drive parameter for the drive part 125. When the result shows that the shape of the IOL 2 is not allowable, the controller 300 prohibits advancing of the plunger 121. Namely, the controller 300 of the present embodiment determines the drive parameter for pushing out the IOL 2 according to the shape of the IOL 2.

Figure 6A:
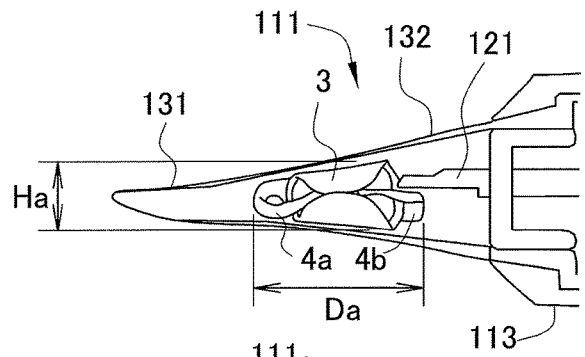
FIG. 6A is an explanatory view explaining determination of a shape of the intraocular lens.
Figure 6B:
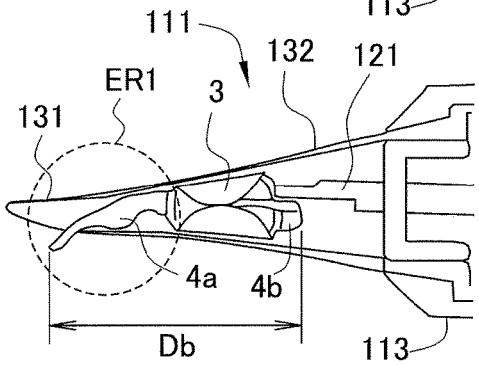
FIG. 6B is an explanatory view explaining determination of the shape of the intraocular lens.
Figure 6C:
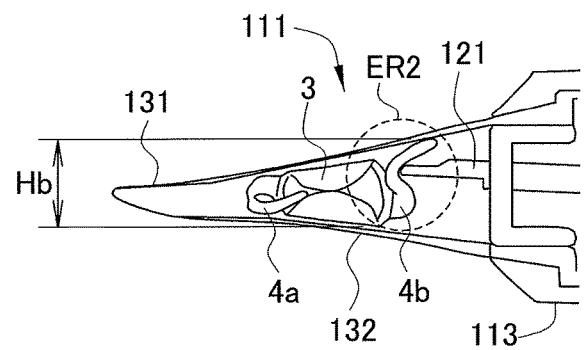
FIG. 6C is an explanatory view explaining determination of the shape of the intraocular lens.

FIGS. 6A to 6C are examples each showing the shape of the IOL 2 which is determined by the controller 300. Each of the FIGS. 6A to 6C shows the shape of the IOL 2 which has reached the waiting position. FIG. 6A shows one shape (deformed shape) of the IOL 2 which is determined to be in the allowable shape by the controller 300 of the present embodiment. FIGS. 6B and 6C show shapes (deformed shapes) of the IOL 2 which are each determined not to be in the allowable shape by the controller 300 of the present embodiment.

The shape of the IOL 2 having reached the waiting position in FIG. 6A is illustrated such that the distal end of the front-side support part 4a and the distal end of the rear-side support part 4b are placed on the optical part 3 (placed inside the outline of the optical part 3). In other words, the front-side support part 4a and the rear-side support part 4b are tucked on the optical part 3.

The shape of the IOL 2 having reached the waiting position in FIG. 6B is illustrated such that the distal end of the front-side support part 4a extending toward the forward (in a leftward direction of the paper in FIG. 6B) of the push-out axis A. In other words, the front-side support part 4a of the IOL 2 in FIG. 6B is not tucked. The IOL 2 in FIG. 6B is in the shape that the distal end of the front-side support part 4a comes out of the tip end of the nozzle portion 131 (see and compare the shape of the IOL 2 in a region ER1 with the shape in FIG. 6A).

The IOL 2 having reached the waiting position in FIG. 6C is in the shape that the distal end of the rear-side support part 4b is directed to the rearward (in a rightward direction of the paper) of the push-out axis A. In other words, the rear-side support part 4b of the IOL 2 in FIG. 6C is not tucked. The IOL 2 in FIG. 6C is in the shape that the rear-side support part 4b is bent in an S-like shape (see and compare the shape of the IOL 2 in a region ER2 with the shape in FIG. 6A).

The controller 300 of the present embodiment detects the shape of the IOL 2 by image processing. Examples of image processing include pattern matching, image binarization, and edge detection. Template data for pattern matching may be recorded on a recording medium (the ROM 362 or the nonvolatile memory 364). As another example, the shape of the IOL 2 may be detected by use of the observed image (the front image IMGf or the tomographic image IMGt) in which a part of the IOL 2 is included.

The controller 300 may determine the shape of the IOL 2 based on whether or not a size of the IOL 2 detected from the front image IMGf is within a predetermined size. Specifically, the controller 300 may determine the shape of the IOL 2 based on whether or not a length of the IOL 2 extending in a direction of the push-out axis A is within an allowable range (see and compare a length Da in FIG. 6A with a length Db in FIG. 6B). In another example, the controller 300 may determine the shape of the IOL 2 based on a length of the IOL 2 in a direction orthogonal to the push-out axis A (see and compare a length Ha in FIG. 6A and a length Hb in FIG. 6C).

In the present embodiment, the IOL coming at rest in the waiting position is imaged. As one alternative, the IOL 2 which is being pushed out by the plunger 121 (in the moving state) may be imaged to determine the shape of the IOL 2. As another alternative, the IOL 2 which is on the way to move to the waiting position may be imaged. As it will be explained with reference to FIG. 9, the drive parameter (for example, the push-out speed) for pushing out the IOL 2 may be changed according to the shape of the IOL 2.

<Injection of IOL>

Injection of the IOL 2 is now explained with reference to FIGS. 5 to 10. The operator firstly looks into the microscope 205 and injects the injection part 111 into the incision of the patient's eye E. The operator successively operates the IOL injection device 100 to direct the end face of the bevel 131a to the retina. Then, the operator presses down the foot pedal 307 to a second stage (a second inclination angle). The controller 300 detects this pressing of the foot pedal 307 to the second stage and moves (advances) the plunger 121 having been stationed around the waiting position to the forward of the push-out axis A.

When the plunger 121 restarts to move forward, the IOL 2 is further folded into a tiny piece in the tapered portion 132. As the plunger 121 further moves forward, the IOL 2 enters in the nozzle portion 131 and starts to gradually comes out from the tip end of the nozzle portion 131 (see (d) in FIG. 5). The IOL 2 coming out of the nozzle portion 131 gradually restores its original shape. At this time, the controller 300 of the present embodiment controls the push-out speed of the IOL 2 to be at the uniform speed SPD3 (see a section from c to d in FIG. 10) during movement of the IOL 2 from the waiting position to the nozzle portion 131. The IOL 2 is moved at such low speed, and thus the stress applied to the IOL 2 is reduced while the IOL 2 is compressed into a tiny piece (while a sectional area intersecting the push-out axis A is reduced). In the point d in FIG. 10, a half of the IOL 2 comes out of the nozzle portion 131.

As the plunger 121 further moves forward, the front-side support part 4a and the optical part 3 which have come out of the nozzle portion 131 gradually restore their original shapes from the root portion of the rear-side support part 4b. The restored front-face optical surface 3a faces the cornea of the patient's eye E, and the restored rear-face optical surface 3b of the IOL 2 faces the retina of the patient's eye E. When the plunger 121 further moves forward, the IOL 2 is completely injected from the injection part 111 (see (e) in FIG. 5). The plunger 121 of the present embodiment keeps moving after its leading end has come out of the nozzle portion 131 and then stops moving when a protruding amount of the plunger 121 reaches a predetermined amount.

The controller 300 of the present embodiment increases the push-out speed to the speed SPD4 directly after the IOL 2 has come out of the nozzle portion 131. After the push-out speed has once reached the speed SPD4, the controller 300 decelerates the push-out speed from the speed SPD4 (see a section from d to e in FIG. 10). A moving speed of the IOL is expressed by the speed SPD3<the speed SPD4. The push-out speeds are set to a relationship expressed by the speed SPD3<the speed SPD1<the speed SPD4<the speed SPD2. The increase in the moving speed (ejecting speed) of the IOL 2 can prevent the whole or a large part of the IOL 2 from restoring its shape before the IOL 2 injected from the IOL injection device 100 is set in the lens capsule. As a result, after the IOL injection device 100 has injected the IOL 2 into the eye, it is possible to leave out an operation of disposing the IOL 2 having restored its shape in an anterior segment of the patient's eye in the lens capsule. Further, decrease in the push-out speed after increasing to the speed SPD4 lowers the possibility that at least any one of the IOL 2 and the plunger 121 pushes and causes damage to the lens capsule.

As one alternative for the above, the controller 300 may change at least any one of the speeds SPD3 and SPD4. Specifically, the controller 300 may adjust the speed SPD4 of the IOL 2 by analyzing the tomographic image IMGt. To be more specific, the controller 300 analyzes the tomographic image IMGt to detect a distance between the IOL 2 and the lens posterior capsule (see FIG. 7). The controller 300 adjusts the speed SPD4 according to the distance between the IOL 2 and the lens posterior capsule. When the distance between the IOL 2 and the lens posterior capsule is shorter than a predetermined value, the controller 300 controls the moving speed of the IOL 2 to become slower than the speed SPD4. Thus, it is possible to lower the possibility of the IOL 2 pushing the lens capsule and causing damages to the lens capsule. In this case, the predetermined value has been stored in a recording medium (the nonvolatile memory 364 or the like) in advance. When the distance between the IOL 2 and the lens posterior capsule is longer than the predetermined value, the controller 300 controls the moving speed of the IOL 2 to become faster than the speed SPD4. This makes it possible to prevent such a case that the IOL 2 is restored faster than the timing of the IOL 2 entering in the lens capsule.

The controller 300 of the present embodiment detects the deformed state of the IOL 2 while the IOL 2 is being injected from the IOL injection device 100. To be specific, the controller 300 uses the tomographic image IMGt obtained by the tomographic-image imaging optical system 270b to detect the shape of the IOL 2. The controller 300 obtains the tomographic image IMGt during the process of the plunger 121 moving forward (see a step S201 in FIG. 9). The controller 300 detects the shape of the IOL 2 as similar to the above mentioned analysis of the front image IMGf.

The controller 300 of the present embodiment determines a position (a tomographic surface) to obtain the tomographic image IMGt from the front image IMGf. To be specific, the controller 300 makes an analysis of the front image IMGf to detect a direction of the IOL injection device 100. The controller 300 sets the tomographic surface such that the tomographic image IMGt includes the push-out axis A (controls an optical scanner of the tomographic-image imaging optical system 270b).

The controller 300 determines whether or not the IOL 2 is injected from the IOL injection device 100 by the moving position of the plunger 121 or by the tomographic image IMGt (see a step S202 in FIG. 9). When the IOL 2 is injected, the controller 300 controls the external display 306 to display a message of completion of injection (see a step S203 in FIG. 9). When the IOL 2 is not injected, the controller 300 determines the shape of the IOL 2 (see steps S204 and S206 in FIG. 9).

The controller 300 firstly determines whether or not the shape of the IOL 2 is in the allowable shape. This determination may be performed by, for example, determining the allowable or not allowable shape of the IOL 2 as similar to the above mentioned FIGS. 6A to 6C. When the shape of the IOL 2 is not allowable, the controller 300 controls the external display 306 to display the corresponding message (see a step S205 in FIG. 9). As one example, an alarm message to instruct the operator to pull out the injection part 111 which has been injected into the incision may be displayed. As another example, when the IOL 2 is not in the allowable shape, the controller 300 may prohibit the plunger 121 from moving (advancing) (determine the drive parameter).

When the IOL 2 is in the allowable shape, the controller 300 compares the moving position of the plunger 121 with the shape of the IOL 2 to determine the restored state of the IOL 2 (see a step S206 in FIG. 9). The recording member is recorded with the moving position of the plunger 121 associated with data of the shape of the IOL 2 in the corresponding position (recorded in a form of a data table). The controller 300 determines the shape of the IOL 2 in the corresponding position with reference to the data table. The data table is recorded in advance in the recording member (such as the ROM 362) based on experiments, simulations or the like.

When the IOL 2 restores its shape quickly, the controller 300 controls the plunger 121 to move at a low speed (see a step S208 in FIG. 9). Specifically, the controller 300 determines the drive parameter used for driving the drive part 125 and moves the plunger 121 at the low speed. When the shape restoration of the IOL 2 is not quick, the controller 300 controls the plunger 121 to move at a usual speed (see a step S207 in FIG. 9). Specifically, the controller 300 determines the drive parameter used for driving the drive part 125 and moves the plunger 121 at the usual speed.

As mentioned above, the controller 300 controls the plunger 121 to push out the IOL 2, and at the same time, successively adjusts the push-out speed of the IOL 2 according to the shape of the IOL 2. The IOL 2 can be thus prevented from unintentional restoration of its shape. Changes in the moving speed of the plunger 121 enable injection of the IOL 2 in a preferable shape even when the stress applied to the folded IOL 2 is changed.

Figure 7:
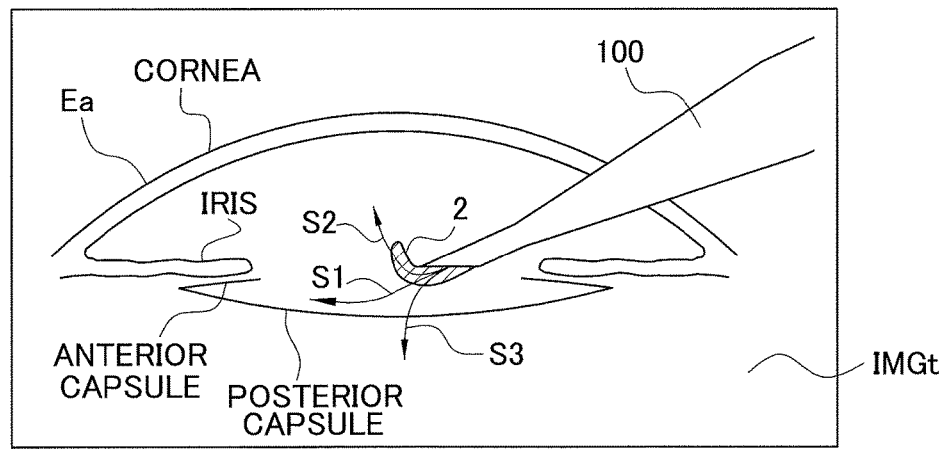
FIG. 7 is an explanatory view explaining an injection direction for injecting the intraocular lens.
Figure 8:
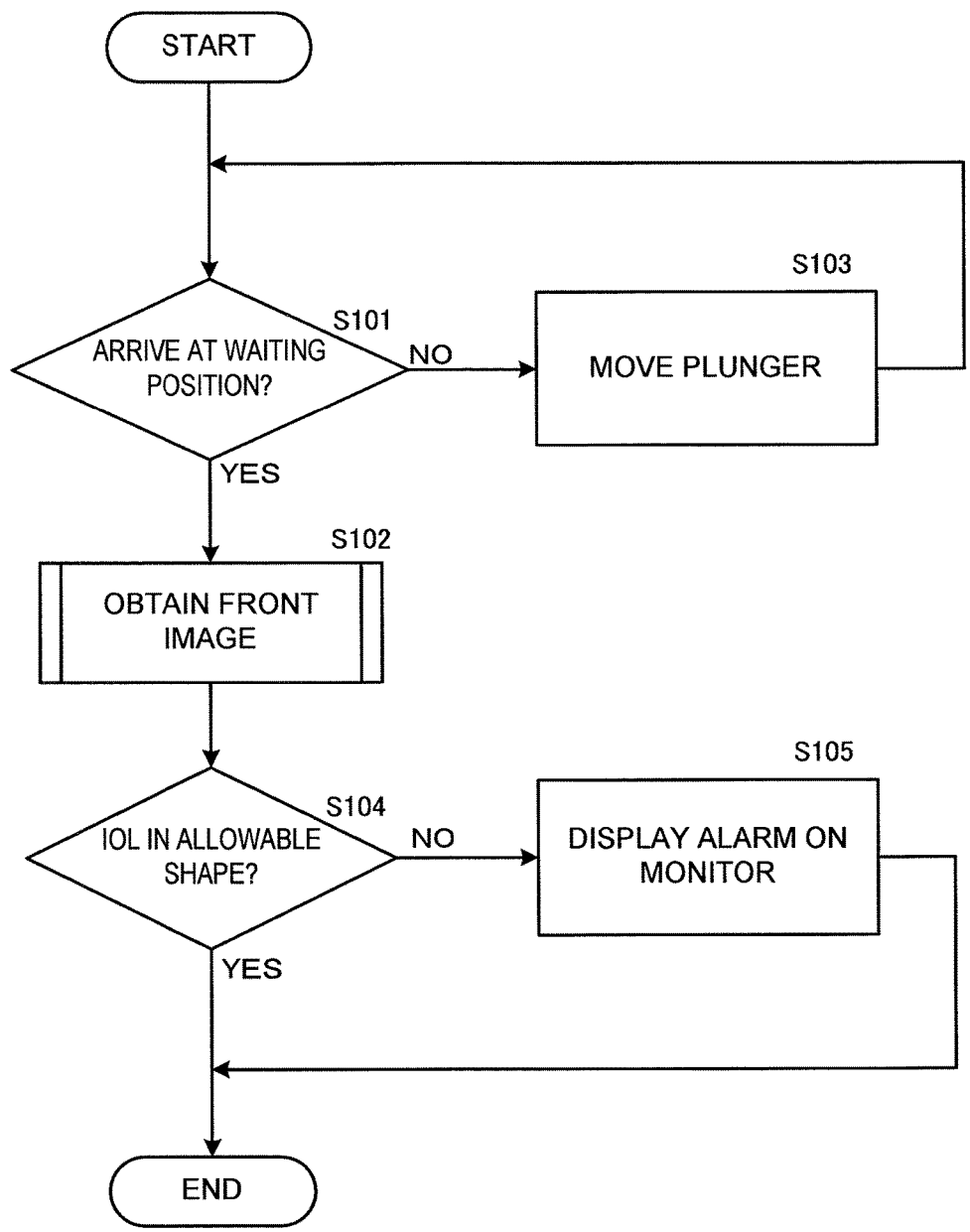
FIG. 8 is a flow chart for injecting the intraocular lens.

FIG. 7 shows a modified example of an operation to determine the shape of the IOL 2 performed by the controller 300. The controller 300 uses image processing to detect an injection direction of the IOL 2 which has come out of the tip end of the nozzle portion 131. The controller 300 determines the moving speed of the plunger 121 according to the detected injection direction. Directions indicated with reference signs S2 and S3 in FIG. 7 are injection directions that the controller 300 of the present embodiment determines as being not allowable.

When the frictional force between the IOL 2 and an inner wall surface defining the hollow portion 140 is locally increased, for example, there is a possibility that the IOL 2 is injected in an unintentional direction (for example, a direction indicated with S2 or S3). The controller 300 detects the injection direction of the IOL 2 and adjusts the push-out speed of the IOL 2 based on the detected result, thus preventing injection in an inappropriate direction due to the above mentioned unbalanced frictional force.

A direction indicated with a reference sign S1 is an injection direction of the IOL 2 which is determined to be allowable by the controller 300 of the present embodiment. When the injection direction of the IOL 2 is not allowable, the controller 300 changes the moving speed of the plunger 121. Injection of the IOL 2 in the direction indicated with the sign S1 facilitates the operation of placing the restoring IOL 2 in the lens capsule of the patient's eye E. Accordingly, the operator's work after injection of the IOL 2 by the IOL injection device 100 can be reduced.

As mentioned above, the controller 300 of the present embodiment detects the shape of the IOL 2 and controls the drive part to push out the IOL 2 based on the detected result. Therefore, even an operator who is inexpert in dealing with the IOL injection device 100 can promptly inject the IOL 2 into the patient's eye E. As one alternative, the controller 300 may detect the stress applied to the IOL 2 (the moving load of the plunger 121) and combine it with the above-mentioned detected deformation result of the IOL 2 to control movement of the plunger 121.

As another alternative, the controller 300 may detect an injection state (such as an injection amount and an injection angle) of the IOL injection device 100 from the observed image. To be specific, the controller 300 analyzes the observed image in which the IOL injection device 100 is included (see FIGS. 2 and 3). The controller 300 detects a center position of a pupil, a position of the incision, and an outline of the IOL injection device 100 to estimate an orientation of the push-out axis A. The controller 300 then determines whether or not the push-out axis A is oriented in an allowable direction. For example, the controller 300 determines whether or not a straight line connecting the incision and the center of the pupil mostly coincides with a direction of the push-out axis A. The controller 300 controls the external display 306 to show a guide to instruct a direction of the push-out axis A (to superimpose the guide on the observed image) based on the determined result.

Figure 11:
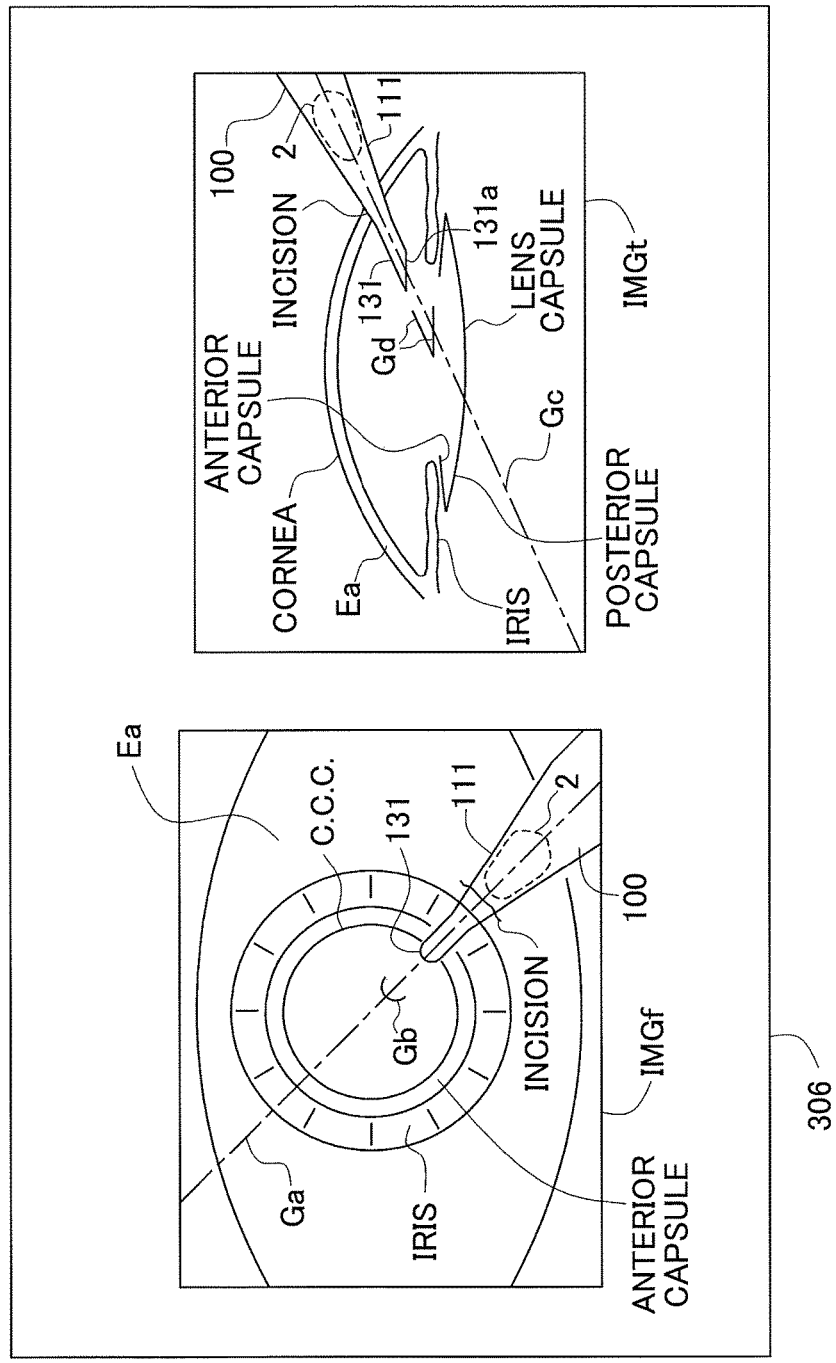
FIG. 11 is an explanatory view explaining a display in a modified example.

FIG. 11 is a modified example of a display image displayed on the external display 306. In this modified example, the controller 300 controls the external display 306 to show both the front image IMGf and the tomographic image IMGt arranged in a row. The controller 300 displays the front image IMGf and the tomographic image IMGt as moving images in this modified example. The controller 300 superimposes guides G (guides Ga to Gd) on the observed image (the front image IMGf or the tomographic image IMGt). Specifically, the controller 300 analyzes the observed image to detect a center position of the pupil and a center position of the incision. The controller 300 draws a line connecting the pupil center and the center of the incision and indicates the guides G on that line. The controller 300 successively analyzes the observed image displayed as moving images and renews the indication of the guides G.

The operator only has to align the guide Ga and the guide Gc with a central axis of the IOL injection device 100. In other words, the guide Ga or the guide Gc is a guiding member to guide a direction of the IOL injection device 100 (i.e., a direction of the push-out axis A). The operator further aligns the guide Gb and the guide Gd with the tip end of the nozzle portion 131. In other words, the guides Gb and Gd are guiding members to guide or direct the injection amount of the IOL injection device 100 injected into the patient's eye E. The guides Gb and Gd in the modified example also direct an orientation of the bevel 131a. When the orientation of the IOL injection device 100 (a circumferential orientation of the push-out axis A) is preferable, the guide Gb (the guide Gd) is aligned with an outline of the nozzle portion 131 which comes in the observed image. In FIG. 11, the IOL injection device 100 is oriented preferably, and therefore the shape of the guide Gb (the guide Gd) is aligned with the shape of the nozzle portion 131. The guides Gb and Gd are guide members to guide or direct the orientation of the IOL injection device 100 (the circumferential orientation of the push-out axis A).

The controller 300 may detect the IOL injection device 100 from the observed image and may give an alarm message (a notification) when the foot pedal 307 is pressed down in an inappropriate position. As another alternative, the controller 300 may control the external display 306 to display an alarm message or may sound an alarm buzzer. As another alternative, the controller 300 may indicate an alignment state of the IOL injection device 100 based on a positional relation (an alignment relation) of the IOL injection device 100 to the guides G. For example, one notification method of the controller 300 is to change colors of the guides G according to an approaching state of the guides G and the IOL injection device 100. As another example, the controller 300 may analyze the observed image and give an audio message to guide an alignment position of the IOL injection device 100.

The guides G enable the operator to place the IOL injection device 100 in a preferable position and inject (eject) the IOL 2 into an eye. Therefore, even if the operator is inexpert in operation of the IOL injection device 100, the IOL 2 can be preferably injected.

As another alternative for the above, the IOL injection system may be provided with a robotic arm and the controller 300 may control this robotic arm. In this example, the controller 300 may displace the IOL injection device 100 (change a position or direction with respect to the patient's eye E) which is held by the robotic arm.

As another alternative, the controller 300 may detect an orientation of the end face of the bevel 131a. Specifically, the controller 300 performs image processing to detect an orientation of the bevel 131a by the tomographic image IMGt in which the IOL injection device 100 is included (see FIG. 3). When the end face of the bevel 131a does not face toward the fundus of the eye, the controller 300 superimposes a guide directing an orientation of the end face of the bevel 131a on the tomographic image IMGt and displays it on the external display 306.

<Operations and Effects>

The IOL injection system 1 of the present embodiment including a push-out member provided with a drive part to push out the soft IOL 2 by use of the drive part, an observation member to obtain the observed image of the IOL 2 which is being pushed by the push-out member, and the determination member to determine the drive parameter of the drive part based on the observed image. The IOL 2 can be thus preferably pushed out. To be specific, a part or the whole of the IOL injection device or a part or the whole of the IOL 2 is observed to determine the drive parameter of the drive part, thus preventing unintentional pushing of the IOL 2. It is therefore possible to prevent a case that the IOL 2 in an unintentional shape is injected into the patient's eye E. As one alternative, the determination member may detect the drive parameter of the drive part by the detection result as well as detecting the shape of the IOL 2 by use of the observed image. Thus, it is further surely possible to prevent injection of the IOL 2 in the unintentional shape into the patient's eye E.

The IOL 2 used for the IOL injection system of the present embodiment includes the optical part 3 and the support parts 4 supporting the optical part 3 in the patient's eye E. The determination member determines the drive parameter taking into account for at least the shape of the support parts 4. Therefore, the IOL 2 can be preferably pushed out even if the IOL 2 includes the support parts 4. In other words, it is possible to prevent such a case that the support part 4 gets untucked during pushing of the IOL 2.

The drive parameter used for the IOL injection system 1 of the present embodiment includes the push-out speed of the IOL 2. Changing the push-out speed of the IOL 2 leads to preferable pushing of the IOL 2. Accordingly, the shape of the IOL 2 can be maintained within an allowable range. Herein, the push-out speed includes halt of pushing.

The observation member included in the IOL injection system of the present embodiment enables to obtain at least any one of the front image IMGf and the tomographic image IMGt of the patient's eye E. Thus, the shape of the IOL can be detected without providing a complicated configuration for the system. In other words, the system can make use of a configuration of a surgical microscope.

The controller 300 for injecting the IOL of the present embodiment is a controller for controlling the IOL injection device, including a first interface to control the drive part to push out the soft IOL 2, a second interface to input the observed image of the IOL 2 which is being pushed by the drive part, and the determination member to determine the drive parameter of the drive part based on the observed image. Thus, the IOL 2 can be preferably pushed out. It is further possible to prevent injection of the IOL 2 in an unintentional shape into the patient's eye E. The controller 300 may be provided in, for example, the IOL injection device 100, a surgical microscope, an apparatus for cataract surgery, or a personal computer.

A method of controlling the IOL injection instrument of the present embodiment includes a first step of inputting the observed image in which at least a part of the IOL 2 is included, a second step of detecting the shape of the IOL 2 by use of the observed image inputted in the first step, and a third step of determining the drive parameter of the drive part to push out the IOL 2 by use of the detection result obtained in the second step. The IOL 2 can be thus preferably pushed out. It is therefore possible to prevent such a case that the IOL 2 in an unintentional shape is injected into the patient's eye E. In the present embodiment, this control method is carried out by a computer in the form of a program. A recording medium of the present embodiment is recorded with this program which is read out by the computer. The observed image does not have to be a precise image but only have to be data related to the observed image.

A configuration of the IOL injection system is not limited to the above. The system may be applied to a case that an IOL (which is sometimes called as a phakic IOL) to be placed in an anterior segment of the patient's eye E (see JP-A-2005-523095 for the phakic IOL, for example).

The IOL injection device 100 of the present embodiment is configured with the cartridge part 101 and the handpiece part 102, but the configuration of the IOL injection device 100 is not limited to this. For example, the device may be applied to a manually operated IOL injection device in which the IOL 2 is pushed out by the force of an operator's hand (for example, an IOL injection instrument described in JP-A-2013-081759). When the controller 300 detects the shape of the IOL 2 as being not appropriate from the front image IMGf and the tomographic image IMGt, an abnormal state may be informed to the operator by the display on the external display 306 and the buzzer.

As another alternative, the push-out member (for example, a plunger) of the IOL injection device to push out the IOL 2 by the force of the operator's hand may be pushed by an actuator provided in the IOL injection system. In the example of the IOL injection system 1 of the present embodiment, instead of the cartridge part 101, an IOL injection instrument (of a manual type) is attached to the handpiece part 102. Specifically, a plunger of the IOL injection instrument (of a manual type) is pushed out by a power-driven member of the handpiece part 102 (for example, a stepper motor). The operator thus chooses manually injecting the IOL 2 without using the handpiece part 102 or not-manually injecting by use of the handpiece part 102 (for example, by electric power).

The IOL injection system 1 of the present embodiment is configured to observe the IOL 2 and determine the drive parameter of the drive part 125 based on the observed shape of the IOL 2. Alternatively, the IOL injection system may only perform the push-out control of the IOL as illustrated in FIG. 10 without adopting the above-mentioned method. Specifically, the controller 300 may change the moving speed of the plunger 121 according to the moving position of the plunger 121 irrespective of the deformed state of the IOL 2. In this example, the IOL injection system may not be provided with the observation member. Thus, for example, the IOL injection system may be configured simply. Such controller to perform the push-out control may be provided in a housing of the IOL injection device. Further, a power source to push out the IOL is not limited to a motor. For example, a gaseous body (such as gas) may be utilized. As another alternative, the push-out speed to push out the IOL may be changed by changing the frictional force applied to the plunger 121.

As another alternative, the IOL injection system may not be provided with the drive part 125 but provided with a guiding member (for example, the guides G in FIG. 11) to guide alignment of the IOL injection device 100 with respect to the patient's eye E. This configuration allows the IOL injection device to be placed in a preferable position for injecting the IOL 2 even by, for example, a manual-type IOL injection device.

The above disclosed embodiments are only illustration in all the aspects and not limitative. The scope of the present invention is defined not by the above explanation but by the appended claims, and the scope of the invention is intended to include the appended claims and any modifications equivalent to and within that scope.

REFERENCE SIGNS LIST

2 Intraocular lens (IOL)
100 IOL injection device
200 Microscope unit
300 Controller

What is claimed is:

1. An intraocular lens injection system comprising:
   a push-out member comprising a drive part, the push-out member configured to push out an intraocular lens by use of the drive part, wherein the intraocular lens comprises an optical part and a support part configured to support the optical part in a patient's eye;
   an observation member configured to obtain an observed image of the intraocular lens which is configured to be pushed out by the push-out member; and
   a controller that determines a drive parameter of the drive part based on the observed image,
   wherein the controller is configured to determine the drive parameter according to at least a shape of the support part.

2. The intraocular lens injection system according to claim 1, wherein the drive parameter includes a push-out speed for pushing out the intraocular lens.

3. The intraocular lens injection system according to claim 1, wherein the observation member is configured to obtain at least any one of a front image and a tomographic image of the patient's eye.

4. A controller for controlling an intraocular lens injection device comprising:
   a first interface configured to control a drive part configured to push out an intraocular lens, wherein the intraocular lens comprises an optical part and a support part configured to support the optical part in a patient's eye;
   a second interface configured to input an observed image of the intraocular lens which is configured to be pushed out by the drive part; and
   wherein the controller is further configured to determine a drive parameter of the drive part based on the observed image, and
   wherein the controller is configured to determine the drive parameter according to at least a shape of the support part.

5. The controller to control the intraocular lens injection device according to claim 4, wherein the drive parameter includes a push-out speed for pushing out the intraocular lens.

6. The controller to control the intraocular lens injection device according to claim 4, wherein the second interface is configured to obtain at least any one of a front image and a tomographic image of the patient's eye.

* * * * *